(12) United States Patent
Wood et al.

(10) Patent No.: US 9,283,235 B2
(45) Date of Patent: Mar. 15, 2016

(54) INTERMITTENT LOWERING OF CORTISOL AS TREATMENT OF CLINICAL CONDITIONS ASSOCIATED WITH ABNORMAL CONCENTRATIONS OF CORTISOL IN ANIMALS

(75) Inventors: Christopher Wood, Buckinghamshire (GB); George Margetts, Sussex (GB)

(73) Assignee: Stegram Pharmaceuticals Limited, Billinghurst, West Sussex (GB)

( * ) Notice: Subject to any disclaimer, the term of this patent is extended or adjusted under 35 U.S.C. 154(b) by 816 days.

(21) Appl. No.: 10/474,868

(22) PCT Filed: Apr. 9, 2002

(86) PCT No.: PCT/GB02/01653
§ 371 (c)(1),
(2), (4) Date: Apr. 27, 2004

(87) PCT Pub. No.: WO02/080930
PCT Pub. Date: Oct. 17, 2002

(65) Prior Publication Data
US 2004/0204392 A1    Oct. 14, 2004

(30) Foreign Application Priority Data
Apr. 9, 2001  (GB) .................................. 0108865.7

(51) Int. Cl.
| | |
|---|---|
| A61P 5/00 | (2006.01) |
| A61P 5/08 | (2006.01) |
| A61P 5/46 | (2006.01) |
| C07J 71/00 | (2006.01) |
| C07J 41/00 | (2006.01) |
| A61K 31/58 | (2006.01) |

(52) U.S. Cl.
CPC . *A61K 31/58* (2013.01); *C07J 71/00* (2013.01)

(58) Field of Classification Search
CPC .................................. A61K 31/58; C07J 71/00
See application file for complete search history.

(56) References Cited

U.S. PATENT DOCUMENTS

| | | |
|---|---|---|
| 3,296,255 A | 1/1967 | Clinton et al. |
| 3,296,295 A | 1/1967 | Principe et al. |
| 4,029,776 A | 6/1977 | Cafruny et al. |
| 4,062,954 A | 12/1977 | Potts |
| 4,160,027 A | 7/1979 | Christiansen |
| 4,196,188 A | 4/1980 | Besins |
| 4,331,663 A | 5/1982 | Christiansen et al. |
| 4,605,517 A | 8/1986 | Riley et al. |
| 4,717,569 A | 1/1988 | Harrison et al. |
| 4,755,595 A | 7/1988 | Gelotte et al. |
| 4,857,333 A * | 8/1989 | Harold .......................... 424/442 |
| 5,372,996 A | 12/1994 | Labrie |
| 5,550,107 A | 8/1996 | Labrie |
| 5,795,881 A | 8/1998 | Elger et al. |

(Continued)

FOREIGN PATENT DOCUMENTS

| | | |
|---|---|---|
| EP | 0 072 894 A1 | 5/1982 |
| EP | 0 108 606 | 5/1984 |

(Continued)

OTHER PUBLICATIONS

Abstract, Pimenta et al., 2006,Primary aldosteronism: diagnosis and treatment. Journal of clinical hypertension (Greenwich, Conn.*

(Continued)

*Primary Examiner* — Abigail Fisher
(74) *Attorney, Agent, or Firm* — Stites & Harbison PLLC; Richard S. Myers, Jr.

(57) ABSTRACT

Use of a compound of formula (I) or a 3-enol $C_{1-4}$ alkanoate ester thereof in the manufacture of a medicament for the intermittent treatment of a condition of a human or non-human mammal in which said mammal has an abnormally high serum concentration of an adrenal hormone: Wherein $R_1$, $R_2$, $R_5$, and $R_6$ are the same or different and each is hydrogen or C 1 to 4? alkyl; $R_3$ is hydrogen C 1 to 4? alkyl, C 1 to 4? alkenyl or C 1 to 4? alkynyl; $R_4$ is hydroxy, C 1 to 4? alkanoyloxy, a group of formula (II) or (III) Wherein $R_7$ is $(CH_2)_n$, where n is an integer of from 0 to 4, $R_8$ is hydrogen, C 1 to 4? alkyl, hydroxy or $NH_2$ and $R_9$ and $R_{10}$ are the same or different and each is hydrogen or C 1 to 4? Alkyl; or $R_3$ and $R_4$ together are oxo, ethylenedioxy or propylenedioxy. The invention has practical benefits for the treatment of man and other animals with diseases associated with abnormal production of adrenal steroids. The invention also shows that sustained suppression of the adrenal hormones is not required to achieve relief of symptoms in these conditions.

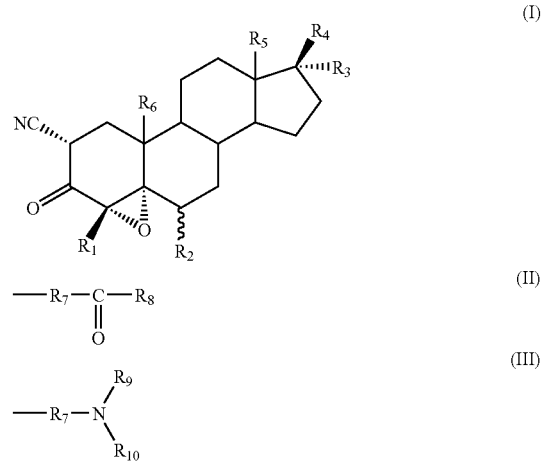

4 Claims, 2 Drawing Sheets

(56) References Cited

U.S. PATENT DOCUMENTS

| | | | |
|---|---|---|---|
| 2001/0008632 | A1 | 7/2001 | Freund et al. |
| 2002/0055512 | A1 | 5/2002 | Marin et al. |
| 2003/0050291 | A1 | 3/2003 | Arad |

FOREIGN PATENT DOCUMENTS

| | | | |
|---|---|---|---|
| EP | 0 108 608 A1 * | 5/1984 | |
| EP | 0108608 | * 5/1984 | |
| EP | 0 142 309 | 10/1984 | |
| EP | 0 154 476 | 9/1985 | |
| GB | 1 123 770 | 8/1968 | |
| GB | 2 010 278 | 6/1979 | |
| GB | 2 130 588 | 6/1984 | |
| GB | 2 155 018 | 9/1985 | |
| GB | 2 345 851 | 7/2000 | |
| WO | WO 01/52833 | 7/2001 | |
| WO | WO 01/87334 | 11/2001 | |
| WO | WO 02/05791 | 1/2002 | |

OTHER PUBLICATIONS

Storr et al. 2007, Paediatric Cushing's Syndrome: epidemiology, investigation and therapeutic advances, TRENDS in Endocrinology and Metabolism, pp. 167-174.*
Abstract, 2007, Feline adrenal disorders, Clinical techniques in small animal practice.*
Abstract, 2007, Primary Aldosteronnism: current knowledge and controversies in Conn's Syndrome, Nature clinical practice. Endocrinology & metabolism.*
Intermittent, http://www.thefreedictionary.com/intermittent, 4 pages. 2010.*
Hurley, 1999, "Trilostane in the treatment of canine hyperdrenocorticism." Poster presented at ESVIM, Vienna on Sep. 1998, ESVIM Newsletter 9(2): 139-142.*
Hess et al. Concurrent disorders in dogs with *Diabetes mellitus*, Journal of the American Veterinarian Medical Association, 271(8):1166-73, 2000.*
Winstanley et al., Br. J. Clin. Pharmac., 1989, 28, 621-628.*
Garnier et al., Laboratory Animals, 1990, 24, 40-43.*
Alivizatos et al., 1993, "Update of hormonal treatment in cancer of the prostate," Anticancer Drugs 4(3):301-309.
Baker et al., 1992, "Oestrogen receptor isoforms, their distribution and relation to progesterone receptor levels in breast cancer samples," Br. J. Cancer 66(6):1083-1087.
Beardwell et al., 1983, "Trilostane in the treatment of advanced breast cancer," Cancer Chemother. Pharmacol. 10(3):158-160.
CAS Printout 1982, 96(5) for McInnes et al., Congr. Eur. Biopharm. Pharmacokinetics, 1:212-221, 1981.
CAS Printout 1978, 88(11)for Rigg et al., Endocrinol. Metab. 45:1261-64, 1977.
Christiansen et al., 1984, "Steroidogenesis Inhibitors. Adrenal Inhibitory and Interceptive Activity of Trilostane and Related Compounds," J. Med. Chem. 27:928-931.
Coombes et al., 1985, "Trilostane therapy for advanced breast cancer," Cancer Treat. Rep. 69(4):351-354.
Drugs of the Future, 1981, 8: 495, "Trilostane".
Fisher et al., 1998, "Tamoxifen for prevention of breast cancer: report of the National Surgical Adjuvant Breast and Bowel Project P-1 Study," J. Natl. Cancer Inst. 90(18):1371-1388.
Geldof et al., 1995, "Inhibition of 3 beta-hydroxysteroid-dehydrogenase: an approach for prostate cancer treatment," Anticancer Res. 15(4):1349-1354.
Hall et al., 1999, "The estrogen receptor beta-isoform (ERbeta) of the human estrogen receptor modulates ER alpha transcriptional activity and is a key regulator of the cellular response to estrogens and antiestrogens," Endocrinology 140(12):5566-5578.
Harmsen et al., 1988, "Endocrine therapy of breast cancer," Eur. J. Cancer Clin. Oncol. 24(7):1099-1116.

Hindley et al., "A Comparison of Two Doses of Trilostane Combined with Dexamethasone in Metastatic Breast Cancer," Proceedings of BACR 25[th] AGM, 252.
Iino et al., 1989, "Effects of trilostane on 7,12-dimethylbenz[a]anthracene-induced rat mammary cancers and body weight of rats in relation to estrogen receptors," Oncology 46(5):301-305.
Ingle et al., 1990, "Evaluation of trilostane plus hydrocortisone in women with metastatic breast cancer and prior hormonal therapy exposure," Am. J. Clin. Oncol. 13(2):93-97.
Komanicky et al., 1978, "Treatment of Cushing's Syndrome with Trilostane (WIN 24,540), an Inhibitor of Adrenanal Steroid Biosynthesis," J. of Clin. Endocrin. and Metab. 47:1042-1051.
Krege et al., 1998, "Generation and reproductive phenotypes of mice lacking estrogen receptor beta," Proc Natl. Acad. Sci. USA 95(26):15677-15682.
Kuiper et al., 1996, "Cloning of a novel receptor expressed in rat prostate and ovary," Proc. Natl. Acad. Sci. USA 93(12):5925-5930.
Loren, G. , 1983, "Aztreonam," Drugs of the Future 8:295-300.
Marsigliante et al., 1991, "Significance of the 8S complex in oestrogen receptor recognition," J. Steroid Biochem. Mol. Biol. 39(5A):703-711.
Maruyama et al., 1998, "A novel isoform of rat estrogen receptor beta with 18 amino acid insertion in the ligand binding domain as a putative dominant negative regular of estrogen action," Biochem. Biophys. Res. Commun. 246(1):142-7.
Pace et al., 1997, "Human estrogen receptor beta binds DNA in a manner similar to and dimerizes with estrogen receptor alpha," J. Biol. Chem. 272(41):25832-25838.
Paech et al., 1997, "Differential ligand activation of estrogen receptors ER alpha and ER beta at AP1 sites," Science 277(5331):1508-1510.
Petersen et al., 1998, "Identification of estrogen receptor beta2, a functional variant of estrogen receptor beta expressed in normal rat tissues," Endocrinology 139(3):1082-1092.
Potts et al., 1978, "Trilostane, an orally active inhibitor of steroid biosynthesis", Steroids 32:257.
Rigg et al., 1977, "Efficacy of intravaginal and intranasal administration of micronized estradiol-17 beta," J. Clin. Endocrinol. Metab. 45(6):1261-1264.
Rubens et al., 1991, "Treatment of metastatic breast cancer and its complications," Curr. Opin. Oncol. 3(6):1029-1034.
Scheinbaum et al., 1981, "Trilostane in hyperadrenocortical states: A summary of clinical studies in the United States," Clin. Pharm. and Therapeutics 29:281.
Schreiber et al., 1989, "Rapid detection of octamer binding proteins with 'mini-extracts', prepared from a small number of cells," Nucleic Acids Res. 17(15):6419.
Takahashi et al., 1990, "Inhibitory effect of synthetic progestins, 4-MA and cyanoketone on human placental 3 beta-hydroxysteroid dehydrogenase/5-4-ene-isomerase activity", J Steroid Biochem. Mol. Biol. 37(2):231-236.
Tueni et al., 1987, "Endocrine effects of Trilostane: in vitro and in vivo studies," Eur. J. Cancer Clin. Oncol. 23(10):1461-1467.
Toueini et al., 1986, Louvain Medical 105(2):111-120. [English Abstract on p. 119].
Wilkinson et al., 1986, "Response of nitrosomethylurea-induced rat mammary tumor to endocrine therapy and comparison with clinical response," Cancer Res. 46(9):4862-4865.
Williams et al., 1993, "Multicentre cross over study of aminoglutethimide and trilostane in advanced postmenopausal breast cancer," Br. J. Cancer 68(6):1210-1215.
Williams et al., 1987, "Multicenter study of trilostane: a new hormonal agent in advanced postmenopausal breast cancer," Cancer Treat. Rep. 71(12)1197-1201.
Braddock JA et al., 2002, "Trilostane and Selegilene evaluated for management of pituitary-dependent hyperadrenocorticism in dogs" BSAVA Congress 2002 Sci Proc:587.
Dewis P, et al., 1983, "Experience with trilostane in the treatment of Cushing's syndrome." Clin. Endocrinol (Oxf). 18(6)533-540.
Eastwood JM, et al., 2001, "Trilostane treatment of four dogs with functional adrenocortical neoplasia." Proc ESVIM Congress 2001:185.

(56) References Cited

OTHER PUBLICATIONS

Harding HR, et al., 1984, "Inhibition of furosemide-induced kaliuresis in the rat by trilostane, an inhibitor of adrenal steroidogenesis." Proc Soc Exp Biol Med. 177(3):388-391.
Hollifield JW, et al., 1975, "Renin-secreting clear cell carcinoma of the kidney." Arch Intern Med. 135(6):859-864.
Huizenga NA, et al., 2000, "Decreased ligand affinity rather than glucocorticoid receptor down-regulation in patients with endogenous Cushing's syndrome." Eur J Endocrinol. 142(5):472-476.
Hurley KJ, "Use of trilostane for treatment of canine hyperdrenocorticism." Poster.
Hurley KJ, 1999, "Trilostane in the treatment of canine hyperdrenocorticism." Poster presented at ESVIM, Vienna on Sep. 1998, ESVIM Newsletter 9(2):11.
Kalmijn S, et al., 1998, "A prospective study on cortisol, dehydroepiandrosterone sulfate, and cognitive function in the elderly. J Clin Endocrinol Metab." 83(10):3487-3492.
Klumer and Clark, (eds.), Clinical Medicine, Ch. 16, p. 815.
Lupien S, et al., 1996, "Longitudinal study of basal cortisol levels in healthy elderly subjects: evidence for subgroups." Neurobiol Aging. 17(1):95-105.
McGowan CM, et al., 2003, "Efficacy of trilostane for the treatment of equine Cushing's syndrome." Equine Vet. J. 35(4):414-418 (accepted Manuscript submitted).
McGowan CM, "Efficacy of trilostane for the treatment of equine-Cushing's disease." Poster.
Milcu SM, et al., 1978, "Cortisol circadian rhythm in 70-100-year-old subjects". Endocrinologie. 16(1):29-39.
Neiger R, 2003, "Treatment of canine hyperadrenocorticism (Cushing's disease) with Trilostane." UK Vet 8(2).
Neiger R, et al., 2000, "Long term efficacy and safety of trilostane for treatment of canine hyperdrenocorticism." J Vet Int Med 14:376.
Neiger R, et al., 2002, "Trilostane treatment of 78 dogs with pituitary-dependent hyperadrenocorticism." Vet Rec. 150(26):799-804.
Neiger R, et al., 2001, "24 hour cortisol values in dogs with hyperadrenocorticism on trilostane". Poster, BSAVA Congress.
Neiger R, et al., 2003, "Owner's perceptions of trilostane therapy for hyperdrenocorticism." BSAVA 2003 Congress Proc: 526.
Nishizawa S, et al., 1999, "What can predict postoperative 'endocrinological cure' in Cushing's disease?." Neurosurgery. 45(2):239-244.
Oakley RH, et al., 1997, "Expression and subcellular distribution of the beta-isoform of the human glucocorticoid receptor." Endocrinology. 138(11):5028-5038.
Oakley RH, et al., 1999, "The dominant negative activity of the human glucocorticoid receptor beta isoform. Specificity and mechanisms of action." J Biol Chem. 274(39):27857-27866.
Overend M, 2003, "Canine Cushing's syndrome: a case report." Vet Rev Feb. 21-24, 2003.
Ramsey I, et al., 2001, "The effect of trilostane on ACTH stimulation tests performed at two different timed post treatment." Proc ESVIM Congress 2001:184-185.
Ruckstuhl NS, et al., 2001, "Clinical, laboratory and ultrasonographic findings in dogs with pituitary-dependent hyperadrenocorticism druing trilostane treatment." Proc ESVIM Congress 2001:140.
Ruckstuhl NS, et al. 2002, "Results of clinical examinations, laboratory tests, and ultrasonography in dogs with pituitary-dependent hyperadrenocorticism treated with trilostane." Am J Vet Res. 63(4):506-512.
Starkman MN, et al., 1992, "Hippocampal formation volume, memory dysfunction, and cortisol levels in patients with Cushing's syndrome." Biol Psychiatry. 32(9):756-765.
Van Cauter E, et al., 1996, "Effects of gender and age on the levels and circadian rhythmicity of plasma cortisol." J Clin Endocrinol Metab. 81(7):2468-2473.
Yamaguchi Y, et al., 1998, "Reduced serum dehydroepiandrosterone levels in diabetic patients with hyperinsulinaemia." Clin Endocrinol (Oxf). 49(3):377-383.
Petrus et al., entitled "Use of Trilostane for the Treatment of Pituitary-Dependent Hyperadrenocorticism in a Cat," *Journal of Small Animal Practice*, vol. 44: pp. 269-272 (2003).
Mantis et al., entitled: "Changes in Ultrasonographic Appearance of Adrenal Glands in Dogs Wit Pituitary-Dependent Hyperadrenocorticism Treated With Trilostane," *Veterinary Radiology & Ultrasound*, vol. 44:6, pp. 682-685 (2003).
Witt et al., entitled: "Adrenocorticotropic Hormone Levels in Dogs with Pituitary-Dependent Hyperadrenocorticism Following Trilostane Therapy," *Veterinary Record*, 154: pp. 399-400 (2004).
Armanini et al., entitled: "Regulation of Corticosteroid Receptors in Patients with Anorexia Nervosa and Cushing's Syndrome," *Journal of Endocrinology*, 158: pp. 435-439 (1998).
Kirk et al., entitled: "Cushing's Disease: Clinical Manifestations and Diagnostic Evaluation," *American Family Physician*, (Sep. 1, 2000).
McGowan et al., entitled: "Efficacy of Trilostante in the Management of Equine Cushing's Disease," *J. Vet. Intern. Med.* vol. 15 p. 322, ACVIM Abstracts, 202 (2001).
*Med. Lett.. Drugs Therapy*, 27(698), 87-88 (1985).
Proceedings of the 16$^{th}$ annual AAVD & ACVD Meeting, Apr. 4-9, 2001, Norfolk Virginia; "The use of trilostane for the treatment of alopecia X in Pomerians and miniature poodles."
Cerundolo R., 2001, "The use of trilostane for the treatment of alopecia X in Pomerians and miniature poodles," *Veterinary Dermatology* 12:225-241.
Ronald de Kloet et al., 1998, "Brain Corticosteroid Receptor Balance in Health and Disease," *Endocrine Reviews* 19(3):269-301.
Kintzer and Peterson, 1991, "Mitotane (o.p'-DDD) Treatment of 200 Dogs with Pituitary-Dependent Hyperadrenocorticism," *Journal of Veterinary Internal Medicine* 5:182-190.
Rijnberk and Belshaw, 1988, "An alternative protocol for the medical management of canine pituitary-dependent hyperadrenocorticism," *The Veterinary Record 122*:486-488.
Lubberink and Voorhout, 1989, "Diagnosis and treatment of canine Cushing's syndrome," *Tijdschrift voor diergeneeskunde 114*(1):37S-39S.
Hertog et al., 1999, "Results of non-selective adrenocorticolysis by o.p'-DDD in 129 dogs with pituitary-dependent hyperadrenocorticism," *The Veterinary Record 144*:12-17.
Ltüdecke et al., 2001, "Cushing's disease: a surgical view," *Journal of Neuro-Oncology 54*:151-166.
Nieman, L.K., 2002, "Medical Therapy of Cushing's Disease." *Pituitary* 5:77-82.
Mahmoud-Ahmed and Suh, 2002, "Radiation Therapy for Cushing's Disease: A Review," *Pituitary 5*:175-180.
The ESVIM Newsletter, 1999, vol. 9(2):1-28.
Hurley et al., 1998, "The Use of Trilostane for the Treatment of Hyperadrenocorticism in Dogs," Proceedings of the 16$^{th}$ Annual Veterinary Medical Forum, San Diego, CA: 51.
Johnston et al., 2005, "Absorption of Trilostane in the Fasted and Non-Fasted Healthy Dog," Proceedings 15th ECVIM Congress: 223.

* cited by examiner

INTERMITTENT LOWERING OF CORTISOL AS TREATMENT OF CLINICAL CONDITIONS ASSOCIATED WITH ABNORMAL CONCENTRATIONS OF CORTISOL IN ANIMALS

FIELD OF THE INVENTION

The present invention relates to the use of a group of chemically active compounds to cause intermittent lowering of blood concentrations of adrenal hormones and thereby treat the symptoms of clinical conditions associated with the abnormal concentrations of such hormones. Previously accepted medical and veterinary protocols for treatment required the sustained lowering of serum concentrations of these hormones in order to achieve a clinical response.

BACKGROUND OF THE INVENTION

An increased production of hormones by the adrenal glands is responsible for a variety of clinical conditions in man and other animals. Prolonged exposure of every tissue in the body to an excess of cortisol produces Cushing's syndrome (CS). Endogenous causes of Cushing's syndrome are (1) adrenocorticotropin (ACTH)-dependent, including Cushing's disease—the hypercortisolism that results form the excessive secretion of corticotropin (ACTH) by a pituitary adenoma, ectopic ACTH-producing tumours. Corticotropin releasing hormone (CRH)-producing tumours, and (2) ACTH-independent Cushing's syndrome, including cortisol-producing adrenal benign or malignant tumours, and rare adrenal hyperplasia. The incidence of ACTH-dependent Cushing's syndrome due to endogenous causes is about 60%, in which autonomous pituitary ACTH secretion is responsible for 95%, and the rest are ectopic ACTH-producing tumours. Cortisol-secreting tumours are responsible for about 40% of endogenous causes, in which benign adenoma is 90% and adrenocortical carcinoma is approximately 10%.

The classical symptoms of Cushing's syndrome include central (abdominal) weight gain and a typical change in appearance, thinning of the skin, muscle weakness, amenorrhoea, polyuria and polydipsia, insulin resistance, hypertension, depression, psychosis and insomnia. In addition patients with chronic hypercortisolaemia due to Cushing's syndrome may exhibit cognitive dysfunction in a pattern similar to that seen in Alzheimer's disease (Starkman M N et al *Biol Psychiatry* 1992 Nov. 1; 32(9):756-65). Many of the changes seen in Cushing's syndrome are very similar to those seen in the aging process. This has led some to postulate that a raised cortisol level, or an altered responsiveness to glucocorticoids, is responsible, at least in part, for the changes seen in the elderly. It has been suggested that many of the changes seen in the aging process are a form of "pseudo-Cushing's disease".

In a study by Van Cauter et al (*J Clin Endocrinol Metab* 1996 July; 81 (7):2468-73), a total of 177 temporal profiles of plasma cortisol from normal individuals (90 men and 87 women), aged 18-83 years, were analyzed. Twelve parameters quantifying mean levels, value and timing of morning maximum and nocturnal nadir, circadian rhythm amplitude, and start and end of quiescent period were calculated for each individual profile. In both men and women, mean cortisol levels increased by 20-50% between 20-80 years of age. Premenopausal women had slightly lower mean levels than men in the same age range, primarily because of lower morning maxima. The level of the nocturnal nadir increased progressively with aging in both sexes. An age-related elevation in the morning acrophase occurred in women, but not in men. The diurnal rhythmicity of cortisol secretion was preserved in old age, but the relative amplitude was dampened, and the timing of the circadian elevation was advanced. They concluded that there are marked gender-specific effects of aging on the levels and diurnal variation of human adrenocorticotropic activity, consistent with the hypothesis of the "wear and tear" of lifelong exposure to stress. They suggested that the alterations in circadian amplitude and phase could be involved in the etiology of sleep disorders in the elderly. However, the rise in cortisol levels may not be a universal feature in the elderly as indicated by the study from Lupien et al (*Neurobiol Aging* 1996 January-February; 17(1):95-105) in which a group of 51 healthy elderly volunteer subjects participated in a 3- to 6-year longitudinal study of basal cortisol levels. Cortisol levels were shown to increase with years in one subgroup, to decrease in another, and to remain stable in a third. However, in patients who showed a rise in cortisol levels with time there was a positive correlation between the response to an obsession/compulsion questionnaire and the rate of rise of cortisol. These authors concluded that their results were consistent with animal studies showing the existence of subpopulations of aged rats which differ in hypothalamo-pituitary-adrenal activity and cognitive efficiency.

Not only do cortisol levels tend to rise with age but the circadian rhythm of cortisol production is also disturbed with the passage of years. Milcu et al (*Endocrinologie* 1978 January-March; 16(1):29-39) examined the circadian rhythms of plasma cortisol in 25 persons aged between 70 and 100 years and compared them with 5 persons aged between 17 and 38 years. The results showed that the circadian rhythm in plasma cortisol changes with age. The characteristic phenomena found were a tendency towards reducing the hourly quantitative differences, comparatively more marked between 90 and 100 years; anticipation of the cortisol maximum level of 08.00 hours at 04.00 hours in the group of 71 to 80 years, and at 00.00 hours in some of the subjects older than 80. A normal circadian rhythm was found in 2 of the 25 cases examined. The changes in the circadian rhythms of cortisol showed that the regulation systems are also impaired in the aging process. It is possible that early-morning insomnia of the aged may be due to this anticipation in cortisol secretion Because glucocorticoid excess is associated with hippocampal damage in animals, and the hippocampus participates in learning and memory, the relationships between hippocampal formation (HF) volume, memory dysfunction, and cortisol levels was explored in 12 patients with Cushing's syndrome. After magnetic resonance imaging, HF volume was determined using digital sum of track ball traces of denrate gyrus, hippocampus proper and subiculum, correcting for total intracranial volume. For 25% of the patients, HF volume fell outside the 95% confidence intervals for normal subject volume given in the literature. In addition, there were significant and specific correlations between HF volume and scores for verbal paired associate learning, verbal recall, and verbal recall corrected for full-scale IQ ($r=0.57$ to $0.70$, $p<0.05$). HF volume was negatively correlated with plasma cortisol levels ($r=-0.73$, $p<0.05$). These studies suggest an association between reduced HF volume, memory dysfunction, and elevated cortisol in patients with CS.

Thus, the changes seen in patients with CS are thought to be due to the harmful effects of elevated cortisol levels. The treatment of CS is based on reducing the raised cortisol levels, either by removing the source of the increased production or by blocking the synthesis of cortisol in the adrenal. The aim is to reduce the mean level during the day to 300-400 nmol/L, equivalent to normal production (Internal Medicine 2$^{nd}$ edition, editors J Kumar and M L Clark chapter 16 pg. 815).

Cushing's disease occurs in many animal species as well as man. In dogs the disease is characterised by weight gain, lethargy, diabetes, coarse thickening of the hair, polyuria and polydipsia. It is perhaps a more common disease in certain breeds of dog than it is in humans.

In certain breeds of dogs changes in adrenal and/or gonadal hormone levels can cause a form of adult-onset alopecia, Alopecia X. The link of this disease with adrenal hormone abnormalities has been well established, with the condition also being called congenital adrenal hyperplasia, Cushing's-like syndrome and adult onset hyposomatotropism. Affected dogs are healthy except for hair and skin changes. Alopecia X occurs mostly commonly in the Nordic breeds, dogs such as pomeranians, chow chow, Irish water spaniels, husky and poodles. Alopecia usually develops in young adult dogs between 1 and 2 years of age and can occur in either sex. A symmetrical pattern of hair loss over the trunk and thighs is typical and may be associated with intense hyper-pigmentation. The hormonal abnormalities associated with Alopecia X vary between the breeds; altered steroidogenesis occurs in affected miniature poodles and Pomeranians with increased blood and urinary cortisol and 17 hydroxy progesterone (17 OHP) concentrations. In alopecic keeshonds there is an increased blood 17 OHP and oestradiol level. In alopecic chows and Irish water spaniels there are increased concentration of 17 OHP.

Horses, especially elderly horses, can also develop an equine variety of CS. This is characterised by polyuria, polydipsia, lethargy and peri-orbital fat deposits. A significant proportion of horses with CS also develop laminitis, a condition that affects the small bones of the feet and which can be notoriously difficult to treat. The aim of treatment in animals is the same as in humans and attempts to achieve a permanent suppression of the raised cortisol levels.

According to Nishizawa S, et al (*Neurosurgery* 1999 August; 45(2):239-44) the goal of surgical treatment for Cushing's disease is "endocrinological cure." In this study postoperative endocrinological analysis was evaluated in 18 patients with Cushing's disease who underwent trans-sphenoidal surgery. Serum adrenocorticotropic hormone (ACTH) levels were measured by radioimmunoassay during the first week after surgery. One week after surgery, a test using corticotropin-releasing hormone (CRH) was performed on each patient to check the reserve function of normal ACTH-secreting cells. In eight patients, postoperative ACTH levels were below the measurable level of 1 week, and ACTH showed no response to the CRH test. In these patients serum ACTH and cortisol levels were kept in the normal range with a normal diurnal variation during long-term follow-up. These patients were defined as endocrinologically cured. In seven patients the ACTH level returned to within normal range on the day after surgery but ACTH was provoked by the CRH test. Five of these seven patients showed subsequent re-elevation of ACTH above the normal range. ACTH levels were never normalized in the remaining three patients, and medical treatments were unavoidable. The study's authors defined endocrinological cure in Cushing's disease as a lack of response of ACTH to the CRH test in the early post-operative stage and an unmeasurably low ACTH level in the week after surgery. Obtaining a normal range of ACTH level postoperatively was insufficient to define endocrinological cure.

An essential element of treatment has therefore been the complete eradication of the ACTH drive or the extirpation of the source of increased cortisol production. This nowadays is usually achieved by surgical removal of the adrenal glands or by destroying the pituitary lesion responsible for the increased ACTH production. If the increased ACTH is from an ectopic site the principle remains the same i.e. removal of the source of ACTH. For all such treatments to be successful there is a resulting sustained fall in cortisol levels and patients may be required to receive hormonal supplements.

SUMMARY OF THE INVENTION

The unexpected finding of this invention is that the active compounds of the invention are capable of relieving symptoms and effectively treating conditions associated with abnormal concentrations of adrenal hormones in the blood whilst only lowering the elevated serum hormone concentrations for a short period of time and not over a sustained period of the 24 hours of each day. This effect can be produced by giving intermittent doses of the active agents, usually only once per day.

In particular, the intermittent lowering of serum hormone concentrations was effective in treating Cushing's disease and associated conditions and Alopecia X in dogs.

Accordingly the invention provides:

use of a compound of formula (I) or a 3-enol $C_{1-4}$ alkanoate ester thereof in the manufacture of a medicament for the intermittent treatment of a condition of a human or non-human mammal in which said mammal has an abnormally high serum concentration of an adrenal hormone:

wherein $R_1$, $R_2$, $R_5$ and $R_6$ are the same or different and each is hydrogen or $C_{1\ to\ 4}$ alkyl;

$R_3$ is hydrogen, $C_{1\ to\ 4}$ alkyl, $C_{1\ to\ 4}$ alkenyl or $C_{1\ to\ 4}$ alkynyl;

$R_4$ is hydroxy, $C_{1\ to\ 4}$ alkanoyloxy, a group of formula (II) or (III)

wherein $R_7$ is $(CH_2)_n$ where n is an integer of from 0 to 4, $R_8$ is hydrogen, $C_{1\ to\ 4}$ alkyl hydroxy or $NH_2$ and $R_9$ and $R_{10}$ are the same or different and each is hydrogen or $C_{1\ to\ 4}$ alkyl;

or $R_3$ and $R_4$ together are oxo, ethylenedioxy or propylenedioxy.

DETAILED DESCRIPTION OF THE INVENTION

A novel concept embodied in this invention is that relief of the symptoms of Cushing's syndrome, whether ACTH-dependent or ACTH-independent, can be achieved by intermittent lowering of the cortisol levels. This approach differs significantly from the established therapies in that it allows production of cortisol and other related hormones to be blocked for a period of only a few hours each day rather than prolonged or permanent blockade of cortisol production. This has specific advantages for the patient in that it provides a successful method of medical control of adrenal hypersecretion and obviates the need for surgical ablation of the adrenals and long-term hormonal supplementation.

Compounds of the Invention—Trilostane and Related Compounds and their Properties The present invention is concerned primarily with compounds having the general structure $2\alpha$-cyano-$4\alpha,5\alpha$-epoxyandrostan-$17\beta$-ol-3-one. The compound of the above formula has the common name "trilostane" and is described in British Patent Specification No. 1,123.770 and in the U.S. Pat. No. 3,296,295. The compounds described in this invention are based around the trilostane molecule but the claims refer also to related compounds such as the first metabolite of trilostane, ketotrilostane, and other similarly related compounds, such epostane. The earlier Specifications describe the adrenocortical inhibiting properties of trilostane and related compounds. In British Patent Specification No. 2,130,588 an improved method of manufacture for trilostane and related compounds was described. This allowed the micronising of the compounds to particles having a mean equivalent sphere volume diameter of between 5-12 μm, with at least 95% of the particles having a particle size of less than 50 μm. The greater specificity of particle size improved the bioavailability of trilostane and controlled the amount of active metabolite formed thus improving the clinical response and decreasing variability of earlier preparations. Trilostane has been extensively studied as a treatment of advanced breast cancer. Several published studies confirm the efficacy of trilostane with response rates of between 29% (Williams C. J. et al, Brit.J.Cancer (1993)68, 1210-1215) and 38% (Ingle J. N. et al, Am.J.Clin.Oncol., 1990, 13(2), 93-97). In all the previous work with trilostane it was believed that the mode of action was by competitive inhibition of the $3\beta$-hydroxysteroid dehydrogenase enzyme system. The action was thought due to androgen depletion and hydrocortisone was given with trilostane to over-ride any feed-back mechanism. The compounds were shown to have no direct action on the then known oestrogen, androgen or progesterone receptors.

However, according to British Patent Application GB 0000984.5 (GB-A-2,345,851) trilostane and related compounds have been shown to have a specific action on some oestrogen receptor isoforms and thereby modulate the receptor and the binding of oestrogen to the receptor(s). Whereas previous claims had been made on the belief, now known to be incorrect, that only one form of the oestrogen receptor existed it is now established that at least two major forms of the oestrogen receptor exist and that trilostane and related compounds specifically modulate ligand binding to these receptors. Whereas the current invention relates to the action of trilostane and related compounds in inhibiting 3 beta dehydrogenase ($3\beta$HSD) activity in the adrenal gland it must be acknowledged that the finding that intermittent lowering of cortisol in animals and humans with hypercortisolaemic states relieves symptoms in such conditions may not solely be the result of $3\beta$HSD inhibition. It may be that trilostane and related compounds modulate binding of cortisol and other related hormones to the glucocorticoid receptors and that the prolonged relief of symptoms seen with intermittent (once daily) treatment with trilostane may bear little or no relation to the level of cortisol reached in the serum but be more related to the sustained or extended effect on the appropriate receptor. Alternatively, the lowering of cortisol levels for a limited period each day rather than the sustained lowering achieved by adrenalectomy or continuous medical therapy may have a beneficial effect by altering ligand affinity at the glucocorticoid receptor. In a study by Huizenga N A et al (*European Journal Endocrinology* 2000; 142(5):472-6) showed that the mechanisms of action of glucocorticoids (GCs) are mediated by the intracellular glucocorticoid receptor (GR) and a significantly lower ligand affinity was identified in cells from patients with Cushing's syndrome compared with controls. A complete normalisation of the ligand affinity was observed after treatment in the only patient tested in this respect, whereas the receptor number was not affected. In CS patients, there was a statistically significant negative correlation between cortisol concentrations and ligand affinity, which was not found in controls.

These authors concluded that there was a diminished ligand affinity which possibly reflected receptor modification in response to exposure to the continuously high cortisol levels in patients with Cushing's syndrome. This assumption was substantiated by the fact that in one patient a normalisation of the ligand affinity after complete remission of the disease was seen.

Compounds suitable for use in the invention have the formula (I), or are 3-enol $C_{1\,to\,4}$ alkanoate esters thereof.

(I)

wherein $R_1$, $R_2$, $R_5$ and $R_6$ are the same or different and each is hydrogen or $C_{1\,to\,4}$ alkyl;

$R_3$ is hydrogen, $C_{1\,to\,4}$ alkyl, $C_{1\,to\,4}$ alkenyl or $C_{1\,to\,4}$ alkynyl;

$R_4$ is hydroxy, $C_{1\,to\,4}$ alkanoyloxy, a group of formula (II) or (III)

wherein $R_7$ is $(CH_2)_n$, where n is an integer of from 0 to 4, $R_8$ is hydrogen, $C_{1\ to\ 4}$ alkyl, hydroxy or $NH_2$ and $R_9$ and $R_{10}$ are the same or different and each is hydrogen or $C_{1\ to\ 4}$ alkyl;

or $R_3$ and $R_4$ together are oxo, ethylenedioxy or propylenedioxy.

Preferably $R_1$ is hydrogen or methyl and/or $R^2$ is hydrogen or methyl and/or $R_4$ is hydroxy or $R_3$ and $R_4$ together are oxo and/or $R_5$ and $R_6$ are methyl.

More preferably, $R_1$, $R_2$ and $R_3$ are hydrogen, $R_4$ is hydroxy and $R_5$ and $R_6$ are methyl, or $R_1$, $R_3$, $R_5$ and $R_6$ are methyl, $R_2$ is hydrogen and $R_4$ is hydroxy or $R_1$ and $R_2$ are hydrogen, $R_3$ and $R_4$ together are oxo and $R_5$ and $R_6$ are methyl.

Particularly preferred compounds for use in the invention include trilostane itself, its first metabolite ketotrilostane and epostane. Trilostane itself has the formula:

With reference to formula (I), it is preferred that compounds of formula (I) are used wherein $R_1$ is hydrogen or methyl, $R_2$ is hydrogen or methyl and $R_5$ and $R_6$ are methyl. It is further preferred that $R_4$ is hydroxy or $R_3$ and $R_4$ together are oxo. Examples of such preferred compounds are:

Trilostane, wherein $R_1$, $R_2$ and $R_3$ are hydrogen, $R_4$ is hydroxy and $R_5$ and $R_6$ are methyl; keto-Trilostane, wherein $R_1$ and $R_2$ are hydrogen, $R_3$ and $R_4$ together are oxo and $R_5$ and $R_6$ are methyl; and epostane, wherein $R_1$, $R_3$, $R_5$ and $R_6$ are methyl, $R_2$ is hydrogen and $R_4$ is hydroxy.

Treatments of the Invention

General Characteristics:

The claims made in this invention are not limited by the specific mode of action of trilostane and related compounds but refer to the use of these compounds to cause intermittent lowering of serum cortisol, and other related hormone levels rather than the generally accepted practice of sustained cortisol lowering. This is an unexpected finding and one that changes the way in which trilostane and related compounds are administered to animals and patients.

It is relevant to note that two distinct forms of the glucocorticoid receptor have been described recently (Oakley R H et al; *Endocrinology*. 1997:138; 5028-5038) These isoforms have been designated hGRα and hGRβ and it has been shown that hGRβ has a dominant negative activity compared to the positive role of hGRα (Oakley R H et al; *Journal of Biological Chemistry* 1999:274; 27857-27866). This is very similar to the opposing action of the two oestrogen receptors and since the glucocorticoid receptors belong to the superfamily of steroid/thyroid/retinoic acid receptor proteins it is conceivable that trilostane and related compound are having a similar effect on the glucocorticoid receptors to that on the oestrogen receptors.

Also, the inhibition of 3βHSD may take place at the peripheral tissue level as well as in the adrenal gland. Evidence has recently shown that steroid 21- and 11β-hydroxylation may occur in a variety of extra-adrenal human and rat tissues. The synthesis of aldosterone and the transcription of aldosterone synthase mRNA has been demonstrated in rat aortic smooth muscle cells. Aldosterone synthase gives rise to corticosterone and 18-hydroxydeoxycorticosterone. Thus, trilostane and related compounds may exert their action by inhibiting 3βHSD at extra-adrenal tissue sites such as the brain, skin, bone, arteries etc.

The effects produced by intermittent treatment with trilostane and related compounds may also be the result of altering the ratios of cortisol to its precursors and/or metabolites. Yamaguchi Y et al (*Clin Endocrinol (Oxf)* 1998 September; 49(3):377-83) showed reduced serum dehydroepiandrosterone (DHEA) levels in diabetic patients with hyperinsulinemia. DHEA is a precursor of cortisol and serum levels are known to be increased after trilostane administration. Since up to 90% of patients with cortisol hypersecretion are glucose intolerant and diabetes is a feature of Cushing's syndrome the ratio of cortisol to DHEA and other precursors may be very relevant.

Furthermore, a prospective study was performed by Kalmijn S, et al (*J Clin Endocrinol Metab* 1998 October; 83(10): 3487-92) to investigate the relation between the peripheral concentrations of the adrenal steroid hormones cortisol and dehydroepiandrosterone sulfate (DHEAS) and cognitive impairment and decline. The study population consisted of a sample of 189 healthy participants from the population-based Rotterdam Study, aged 55-80 years. Fasting blood levels of DHEAS before dexamethasone administration and of cortisol and corticosteroid-binding globulin before and after the administration of 1 mg dexamethasone overnight were determined. The 30-point Mini-Mental State Examination (MMSE) was used to assess cognition. The study showed that a 1 standard deviation (SD) increase in the natural logarithm of cortisol after the administration of 1 mg dexamethasone (SD=0.68) was associated with an odds ratio (OR) for cognitive decline of 1.5 (95% CI, 1.0-2.3). A 1 SD increase in DHEAS (SD=2.10 micromol/L) was inversely, but non-significantly, related to cognitive impairment (OR=0.5; 95% CI, 0.2-1.1) and cognitive decline (OR=0.6; 95% CI, 0.4-1.1). The concentration ratio of free cortisol over DHEAS was significantly related to cognitive impairment (OR=1.8; 95% CI, 1.0-3.2). This prospective study among healthy elderly subjects suggested that basal free cortisol levels were positively related to cognitive impairment, and cortisol levels after dexamethasone treatment were related to cognitive decline. There was an inverse, but nonsignificant, association between DHEAS and cognitive impairment and decline.

Treatment Goals

In one embodiment (see Example 2, for example), the present invention provides means of lowering levels of one or more adrenal hormone. Preferably, said hormone, or one of said hormones, is cortisol. According to this embodiment, treatments of the invention preferably act by lowering production of cortisol and/or other adrenal hormones.

According to this embodiment, levels of one or more adrenal hormone are lowered on an intermittent basis. Previously accepted clinical and veterinary practice has been directed towards continual reduction in such levels, which has undesirable consequences as discussed above.

Levels may be lowered to any reduced level that gives partial or total relief, preferably total relief, from the condition in question. Since this invention applies to more than one condition and more than one species, the desired level may vary, and a person of skill in the art will be able to define an appropriate level and devise a dosage regimen accordingly. In particular, it is possible to look up or measure levels in normal individuals and devise a dosage regimen to reduce levels to or towards, the normal range. This can be done by calculation, experiment or a combination of the two. The Examples of the present application can be used as guidance.

For example, adrenal hormone levels, eg cortisol levels, may be reduced to less than 90%, less than 80%, less than 70%, less than 60% or less than 50% of the elevated pre-treatment levels.

Adrenal hormone levels may be measure by any suitable means. For cortisol, ACTH stimulation tests, TRH stimulation tests and dexamethasone stimulation tests are all possibilities. ACTH stimulation tests are preferred in dogs and TRH or dexamethasone stimulation tests are preferred in horses.

In other embodiments, intermittent administration of compounds of the invention may not actually decrease significantly the level of the adrenal hormone or hormones in question but nevertheless shows a clinical response and provides relief from the symptoms of the condition. See Example 1, for example.

It is believed that compounds of the invention act by one or more of the following mechanisms: blocking adrenal steroidogenesis, by modulation of ligands binding to glucocorticoid receptors, inhibition of 3-beta dehydrogenase at extra-adrenal sites in the body. Treatments may be designed to focus on those goals but the invention is not limited to any particular mode of action.

Conditions to be Treated

The present invention has both medical applications in humans and veterinary applications in non-human mammals. Preferred non-human subjects include horses and dogs.

It is believed that any condition wherein adrenal hormone levels are abnormally elevated may benefit from the intermittent treatment approach of the present invention. Treatment of hypercortisolaemic conditions, in which cortisol levels are abnormally elevated, is preferred. For example, treatments of hypercortisolaemia associated with aging, insulin dependent diabetes, depression, schizophrenia, Alzheimer's disease, Parkinson's disease, alcoholism, anorexia nervosa, bulimia and addiction may be effected according to the invention.

Particularly preferred conditions include Cushing's Syndrome (CS), also known as spontaneous hyperadrenocorticism (HAC), pseudo-Cushing's syndrome. CS may be ACTH-dependent (when it is known as Cushing's disease) or ACTH-independent. Both types are amenable to treatment according to the invention. Further treatable conditions include pituitary dependant HAC and elevated levels of adrenal hormones resulting from adrenal tumours.

Treatment of CS, especially ACTH-dependent CS, in humans, dogs and horses is especially preferred. Treatment of Alopecia X in dogs is also preferred. Treatment of laminitis X in horses is also preferred.

Dosage Regimens

Dosage regimens will be chosen to lower hormone levels to the desired level for an appropriate period of time, or such that intermittent administration gives ongoing relief from symptoms even if hormone levels are not significantly changed. The skilled person will be able to choose appropriate dosage regimens depending on, for example, the condition to be treated, the species of the subject, the size of the subject and the severity of the condition.

As a guide, however, administration will generally be a few times daily, eg once, twice or three or four times daily. Once daily administration is preferred.

Less frequent doses can also be envisaged, e.g. once per two, three or four days, or one per week.

Also as a guide, where serum levels of adrenal hormones are lowered it is preferred that each administration will lead to a lowering of the level over a period of up to one hour, up to two hours, up to four hours or up to six or eight hours. Where administration is once daily, a longer period of lowering (larger dose) may be beneficial, eg once period of up to four, six or eight hours. Conversely, shorter periods (smaller dose) may be preferred for multiple administration, eg up to two or four hours twice daily.

Administration, Dosage and Formulation

Compounds of the invention may be administered in any suitable manner. Oral administration is preferred, eg of a tablet, capsule or suspension formulation. Injection is also a preferred route of administration, especially intravenous administration.

For oral formulations, GB-B-2,130,588 relates to an improved method of manufacture for trilostane and related compounds. This method allows the micronising of the compounds to particles having a mean equivalent sphere volume diameter of from 5 to 12 mm, with at least 95% of the particles having a particle diameter of less than 50 mm. The greater specificity of particle size improves the bio-availability of Trilostane and controls the amount of active metabolite formed, thus improving the clinical response and reducing variability.

Compounds of the invention may accordingly be used in the form of particulate compositions. Such compositions will preferably be micronised compositions.

Particulate compositions for use according to the invention desirably consist of particles having a mean particle diameter of about 12 µm or less and 80, 85, 90, 95% or more, preferably 98% or more, 99% or more or 99.5% or more of the particles have a particle diameter of less than about 50 µm, preferably less than 40 µm, less than 30 µm or less than 20 µm e.g. from 0.1 µm to 10, 20, 30, 40 or 50 µm, 1 µm to 10, 20, 30, 40 or 50 µm or 10 to 20, 30, 40 or 50 µm. The particles preferably have a mean particle diameter of about 5 µm to about 12 µm or of less than about 5 µm, for example from 0.1 to 5 µm or 1 to 5 µm. It is further preferred that the cumulative percentage oversize versus size characteristic curve of the composition exhibits a standard deviation of about 1.5 to 2.5 µm, preferably about 1.75 to 2.25 µm, more preferably about 2 µm, e.g. 1.9 to 2.1 µm.

Dosages will be chosen with treatment goals, dosage regimens and modes of administration in mind, and with particular regard to the size of the subject to be treated.

For oral administration of micronised particle compositions, doses of 10-5000 mg are preferred, more preferably 10 to 1000 mg, 10 to 2000 mg and 10 to 500 mg, more particularly 20 to 500 mg and 30 to 500 mg.

Desirably, the formulation will be coated with a non-toxic pharmaceutical coat or be suspended in a liquid pharmaceutical excipient to render it more palatable and reduce gastric irritation.

For injection, especially intravenous injection, doses may, for example be from 10 to 500 mg, for example 10 to 200 or 10 to 100. A particularly preferred range is 30 to 360 mg.

Regard will however be had to the size of the subject to be treated. Dosages may therefore be measured in mg per kg of bodyweight, eg 0.1 to 20 mg/kg, for example 0.1 to 2, 0.1 to 1 or 0.5 to 1 mg/kg, or up to 2, 5, 10 or 20 mg/kg.

For horses (see Example 1) doses of 0.4 to 1 mg/kg are preferred.

As a guide, dogs of less than 5 kg may be given 30 mg once daily by oral administration, dogs between 5 and 15 kg may be given 60 mg once daily and dogs of greater than 15 kg may be given 120 mg once daily, all to achieve similar effects. Therefore, for dogs of less than 5 kg, doses of 10 to 50, eg 20 to 40 mg are preferred whereas for dogs of 5 to 15 kg, doses of greater than 15 kg, doses of 40 to 80, eg 50 to 70 mg are preferred and for dogs of greater than 15 kg, doses of 100 to 150 mg, eg 110 to 130 mg are preferred.

For any dosage form, suitable pharmaceutical excipients will be chosen, eg sterile water or saline for injections and known capsule, tablet and suspension excipients.

EXAMPLES

Example 1

Ability of Intermittent Administration of Trilostane to Block Adrenal Steroidogenesis The ability of intermittent administration of Trilostane to block adrenal steroidogenesis was assessed in twenty horses (mean age 21, SD 5.7 years) with equine Cushing's disease. The combined dexamethasone suppression thyrotropin releasing hormone (TRH) stimulation test (17 horses) or TRH stimulation test (3 horses) was used as a standard test of function of the hypothalamic-pituitary-adrenal axis. Serum samples for cortisol analysis were collected via indwelling catheter at 4-hourly intervals over 24 hours on each of the test periods. These were before treatment then at 210 minutes (30 min after I mg i.v. TRH) and 22 hours after 40 mg/kg dexamethasone i.m. Affected horses were treated with 0.4 to 1 mg/kg, (mean 0.5 mg/kg) trilostane administered once daily in feed for a period of 30 days. After 30 days endocrine testing was repeated. Serum cortisol before and after treatment was compared by paired t-test.

Polyuria and/or polydipsia, present in 11 horses, was reduced ill all after treatment. Lethargy was present to some degree in 19 horses, but improvement in demeanour was evident in all horses after therapy. Recurrent, chronic or persistent laminitis, present in 17 horses, improved or showed no recurrence in 14 cases. Six horses had phenylbutazone therapy discontinued during the trial due to improvement in lameness attributed to laminitis and 1 horse had phenylbutazone therapy reduced from 2 g to I g daily Three horses showed severe, acute laminitis on presentation, with rotation and sinking evident on radiographs, which did not respond to trilostane. One of these horses was euthanised 14 days into the trial. One horse developed a mild bout of laminitis during the trial (Obel grade 1), but was sound by the time he was re-presented at 30 days.

While baseline cortisol (mean: 141, SD 54 nmol/l) and 22 hours post dexamethasone cortisol (mean; 109, SD 34 nmol/I) in horses before treatment were not significantly different to post treatment [baseline (mean: 159, SD 64 nmol/l), post dexamethasone (mean: 104, SD 48 nmol/l)], there was a significant reduction (p=0.023) of cortisol following TRH administration before (mean: 176. SD 52 nmol/I) and after (mean: 147, SD 61 nmol/I) trilostane.

The results showed that trilostane given once-per-day caused an improvement in most of the clinical signs in all horses, the most consistent being an improvement in demeanour. There was a corresponding decrease in cortisol response to TRH administration although there was no apparent change in cortisol concentrations.

Example 2

Trilostane for the Treatment of Spontaneous Hyperadrenocorticism (HAC)

The use of trilostane for the treatment of spontaneous hyperadrenocorticism (HAC) was evaluated in 11 dogs. The incidence of hyperadrenocorticism (HAC), or Cushing's syndrome, in dogs has been estimated to be around 0.1% and therefore it is a well known entity in veterinary medicine (Chastain et al. 1986). Pituitary dependant hyperadrenocorticism (PDH), which is due to excess adrenocorticotropic hormone (ACTH) production by pituitary corticotrophic adenomas, should be treated by elimination of the ACTH excess. While hypophysectomy is sometimes performed in dogs with PDH (Meji et al. 1998), the operation is not widely available due to its delicate nature. Canine PDH is most often treated with an induction and maintenance dose of the adrenoconicolytic drug o,p'-DDD (mitotane) to which the dog is much more sensitive than other species (Rijinbeck, 1996). Only recently, a new protocol aimed at the complete destruction of the adrenal cortices by a large dose of o,p'-DDD with subsequent replacement of mineral—and glucocorticoids has been advocated (Den Hertog et al.). However, o,p'-DDD, a chemical related to the insecticide DDT, has several side effects in dogs, a high frequency of relapses during therapy, and is not without risk to the owners. In recent years, the efficacy of a number of substances with central or peripheral action has been investigated for treatment of PDH (Bruyette, 1996; Rijbberk et al, 1988; Peterson and Drucker 1978; Stolp et al, 1984, Feldman et al 1990). With the exception of ketoconazole, which predominantly blocks 17,20-desmolase and to a lesser extent 17 alpha-hydroxylase and 11 beta-hydroxylase, efficacy was poor. Furthermore, L-Deprenyl, which has been hypothesised to downregulate ACIH by augmenting dopamine concentration, was recently approved by the American FDA for the treatment of canine PDH. However, a prospective study showed improvement of clinical signs in only 2 of 10 dogs studied (Reusch et al. 1999).

Trilostane, an orally active steroid analogue, has been shown to be a competitive inhibitor of the 3β-hydroxysteroid dehydrogenase enzyme system in animals (Potts et al., 1975) and humans (Komanicky et al, 1978). The drug has been used to modify adrenal steroidogenesis in conditions such as Cushing's syndrome (Dewis et al., 1983), primary aldosteronism (Hollifield et al, 1975) and has also shown to be of benefit in the treatment of breast cancer Williams et al., 1993 Br. J Cancer: 68; 1210-5) in humans. No report exists of trilostane for treatment of canine HAC. For this invention the efficacy of trilostane in dogs with HAC was studied under controlled conditions. Patients were monitored using clinical signs, results of laboratory investigation and the ACTH stimulation test.

Animals were entered into a prospective study and all animals required clinical and laboratory signs of hyperadrenocorticism as well as a final diagnosis of this disease. Data collected from each case included a clinical-history and physical examination, full blood count (CBC), serum biochemical profile, urinalysis and abdominal ultrasound. An ACTH-stimulation test was performed in all dogs. If inconclusive, despite clinical and biochemical suggestion of hyperadrenocorticism, a low-dose dexamethasone suppression test (LDDST) and/or urine cortisol/creatinine ratio were performed, Discriminatory tests, such as a high-dose dexamethasone suppression test (LDDST) or endogenous ACTH levels were done if ultrasound examination of the adrenals was inconclusive. Dogs that had been treated for HAC other medication needed to be off these drugs for at least 10 days. Dogs with renal or hepatic insufficiency and dogs that received steroids were not included in the study.

Dogs were entered into the study sequentially over a period of 2-3.5 years Owners were informed about the experimental nature of the treatment and signed a consent form. The ACTH stimulation test was performed by collection of serum samples before and one hour after intravenous injection of ACTH (Synacthen, Alliance) at a dose of 0.125 mg for dogs weighing less than 15 kg, and 0.25 mg for dogs weighing greater than 15 kg. Cortisol concentration was measured by radioimmunoassay previously validated for dogs Blood for endogenous ACTH was collected into a cooled EDTA tube in ice, centrifuged immediately and the frozen at −20° C. Abdominal ultrasound was performed by an experienced board-certified radiologist and adrenal thickness was assessed as a single measurement made perpendicular to the long axis and was defined as the greatest dorso-ventral dimension.

The following results were considered indicative of HAC: serum cortisol concentration post ACTH stimulation >600 nmol/l; serum cortisol concentration 3 hours post LDDST>50% baseline and 8 hours post LDDST>40 nmol/l; urine cortisol; creainine ratio>$10 \times 10^6$; and bilateral enlargement of the adrenals>7 mm in diameter as determined by ultrasonography. The following results were indicative of adrenal dependant HAC; endogenous ACTH<5.0 pg/ml; serum cortisol concentration 3 and 8 hours post LDDST>50% baseline, and marked unilateral enlargement and distortion of one adrenal gland with contra-lateral compensatory shrunken adrenal gland.

Dogs with pituitary dependant hyperadrenocorticism or adrenal tumour which was unresectable or the owners were unwilling to have surgery performed, respectively, were treated with trilostane. The initial dose for dogs>5 kg was 30 mg once daily, dogs between 5 and 15 kg received 60 mg once daily and dogs>15 kg received 120 mg once daily. Dosages were adjusted based on clinical signs, blood biochemical parameters and an ACTH stimulation test.

Follow-up re-examinations took place after 10 days, 4 weeks, 3 mouths, 6 months and then every 6 months or within 4 weeks of adjusting the dosage. At these points, owners were carefully questioned about their perception of the dogs general well being, dissolution of clinical signs and potential side effects and a physical examination was performed. A full biochemical profile and an ACTH stimulation test were carried out. Further tests such as urinanalysis, urine culture, thoracic radiographs, etc. were done if deemed necessary. If the clinical sips of hyperadrenocorticism (polyuria/polydipsia, polyphagia, exercise intolerance, etc.) were still present and if the post-ACTH cortisol concentration remained above 220 nmol/l, trilostane was given twice daily at the same dosage. If the dog showed side effects or pre and post ACTH cortisol were <40 nmol/l; trilostane was discontinued for two days and the dosage then decreased to the next lower dose range.

A total of 66 dogs, made up of 30 different breeds, were diagnosed with HAC and started on trilostane. The most commonly represented breeds were the cross bred (n=13), the Yorkshire terrier (n=9), and the boxer and Dachshund (each n=4) weighing from 3 to 65 kg (mean SD: 18.9-13.3 kg). Age ranged from 3.5 to 15 years with a mean of 9.6 (2.5) years. Eight dogs were entire females, 25 spayed females, 21 entire males and 12 castrated males. Findings common to all dogs at the beginning or the study were polyuria/polydipsia (n=56), dermatological problems including alopecia, thin skin, hyperpigmentation, or calcinosis cutis (n=34), pot-bellied appearance (n=28) and polyphagia (n=26), while less frequent complaints being exercise intolerance (n=12), panting (n=10) and urinary incontinence (n=8). Two dogs were initially presented for cruciate ligament rupture and one for a non-healing corneal ulcer. Lysodren, given to 4 dogs for three to four days before enrolment into the study, did not show any clinical effect.

At the start of the study the ACTH stimulation test showed an exaggerated response in 45 dogs (serum cortisol post ACTH: range 171-1704; mean 831.8; SD 357.4 nmol/l). Thirty-one dogs had a LDDST performed at the beginning of the study, which showed no suppression in 13 dogs, a gradual and progressive suppression in two dogs, in 10 dogs there was a suppression after 3 hours but this was only transient, while 4 dogs showed a normal, complete suppression after 3 and 8 hours, The HDDST, performed in 15 dogs before enrolment into the study showed rapid onset and consistent suppression in 6 dogs, mild suppression in 4 dogs and no suppression in 5 dogs. Endogenous ACTH was measured in 27 dogs, with a range of <5 to 352 pg/ml (mean 82.0; median 37; SD 95.9). Abdominal ultrasound, done in 58 dogs, showed a unilateral mass in 6 dogs, normal adrenals in 23 dogs and mild unilateral or bilateral adrenalomegaly in 16 dogs. Based on the overall endocrine tests, there were 57 dogs with PDH and 9 dogs with unilateral adrenal tumour.

Trilostane was generally well tolerated by the dogs. Starting dose was between 1.8 and 20 mg/kg (mean: 6.0; SD 3.4 mg/kg). Thirty-seven dogs needed a dose adjustment over the period of their treatment, in 26 dogs the dose was increased to 125 to 900 percent of the starting dose, while 11 dogs had a decrease to 25 to 83 percent of the starting dose, with a mean final dose of 8.2 mg/kg (SD; 5.9 mg/kg). Two cross bred dogs with classical clinical signs and endocrine testing results of HAC were started on 6.5 and 7.5 mg/kg trilostane. While both were well controlled initially, the drug was stopped after two and three months when both showed a flat-lined ACTH stimulation test. One of the dogs also was hyperkalaernic and hyponatraemic (ratio:22.3). In both dogs no more trilostane was given thereafter and the dogs are free of clinical signs after 2.7 and 1.4 years. In the 9 dogs with adrenal tumours, which started on the same dosing protocol as the dogs with PDH, two had the dose halved, three stayed on the original dose while in 4 dogs the dose was increased up to 300% of the original dose.

Before starting trilostane, alkaline phosphatase, alanine amino-transferase and cholesterol values were above normal in 41, 13 and 18 dogs respectively. Two dogs bad a mild azotaemia, while 4 dogs had mildly elevated serum bilirubin. With the exception of the complications outlined below, the following biochemistry abnormalities, all without clinical consequence, were noted during the course of therapy one episode of hyperkalaemia, two episodes of azotaemia, three episodes of hyperbilirubinaemia and two episodes of hypercalcaemia.

Clinical signs of polyuria/polydipsia and polyphagia dissipated within the first 10 days of treatment in 29 dogs and within the first month of treatment in 14 dogs. In 6 dogs clinical signs were improved but these dogs always showed some clinical signs of HAC. In all dogs with skin abnormalities there was marked improvement with normal hair growth 2-3 months after starting of trilostane. At the first re-examination serum cortisol values post ACTH has decreased in all dogs to less than 61% of the original value, and cortisol concentrations remained decreased throughout the entire period the does were receiving trilostane (table 3). Of 54 dogs with PDH, 32 were alive after a mean of 417.3 days (SD 285.2, range 105 to 1120 days) after commencing treatment with trilostane. Twenty-two dogs with PDH were euthanised (n=16) or died at home (n=6) after a mean of 230.9 days (SD: 195.1; range 27-730 days). Three dogs with adrenal tumour remained alive between 200 and 450 days after starting trilostane, while the median survival of the six dogs that died or were euthanised was 260 days (SD: 174.9 days).

Three dogs died acutely at home after an episode of dyspnoea or without any prodromal signs. In all previous re-examinations, these dogs did not reveal any clinical or laboratory abnormalities which could explain their sudden death. One dog was euthanised because of atrial fibrillation. No electrolyte values were evaluated at that time. Finally, two dogs showed hyperkalaemia and hyponatraemia prior to clinical deterioration. In both, trilostane was stopped; however, both dogs were euthanised because of severe arrhythmia or acute renal failure and urinary tract infection.

Example 3

Trilostane in the Treatment of Alopecia X

To study the effect of trilostane in the treatment of Alopecia X a total of 11 dogs with the condition were examined along with 10 unaffected dogs. The hormonal abnormalities were identified, with increases in cortisol and 17 OHP concentrations. Trilostane in a once-daily dose was given to the affected animals. Five of the six Pomeranians (83%) and all four of the Miniature poodles have responded to trilostane, showing hair re-growth in the affected areas.

Example 4

ACTH Stimulation Tests

Dogs with Cushing's disease were given an ACTH stimulation test at 12, 35 and 81 days (average) during a course of treatment with a single daily dose of trilostane of 5-20 mg/kg. The results are shown in Table 3. Cortisol resparse is markedly reduced in the treatment group compared to non-treatment controls. Thus, trilostane has blunted ACTH stimulation of the adrenal gland.

Example 5

Serum Cortisol Levels

In dogs with Cushing's disease, serum cortisol levels were reduced significantly at 4 hrs post daily dosing with trilostane, with some lowering in some dogs at 8 hrs, but return to normal levels thereafter. With this level of lowering there was relief of the symptoms of the Cushing's disease. Results are given in Table 4.

Figure 1:
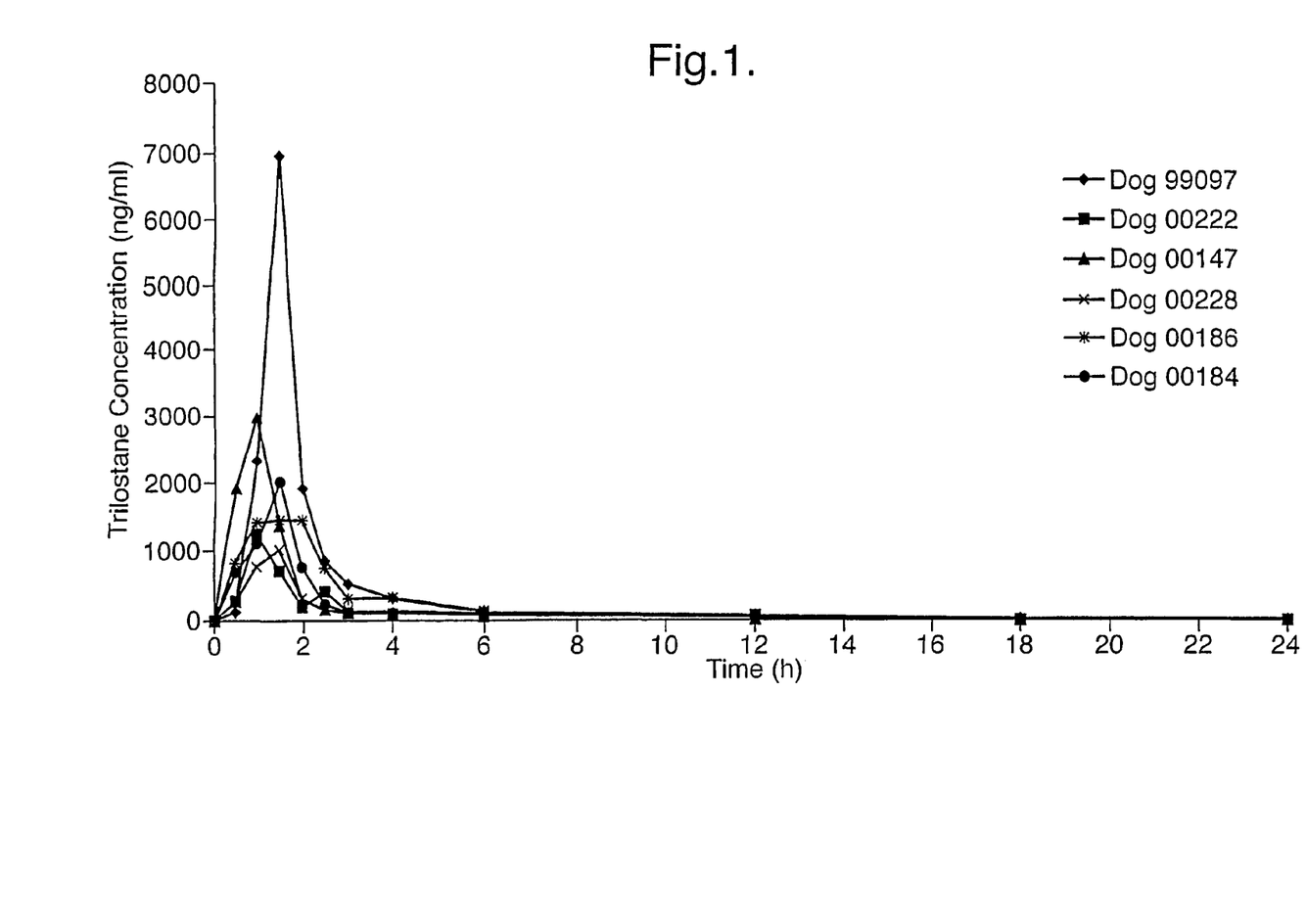
FIG. 1:
Trilostane concentrations in the plasma of 6 dogs: day 0, phase 1 (one 60 mg capsule per day), study no. GB009/01-001.

Serum concentrations of trilostane after single daily dose showing peak at 1-3 hours with rapid elimination thereafter are shown in FIG. 1.

Figure 2:
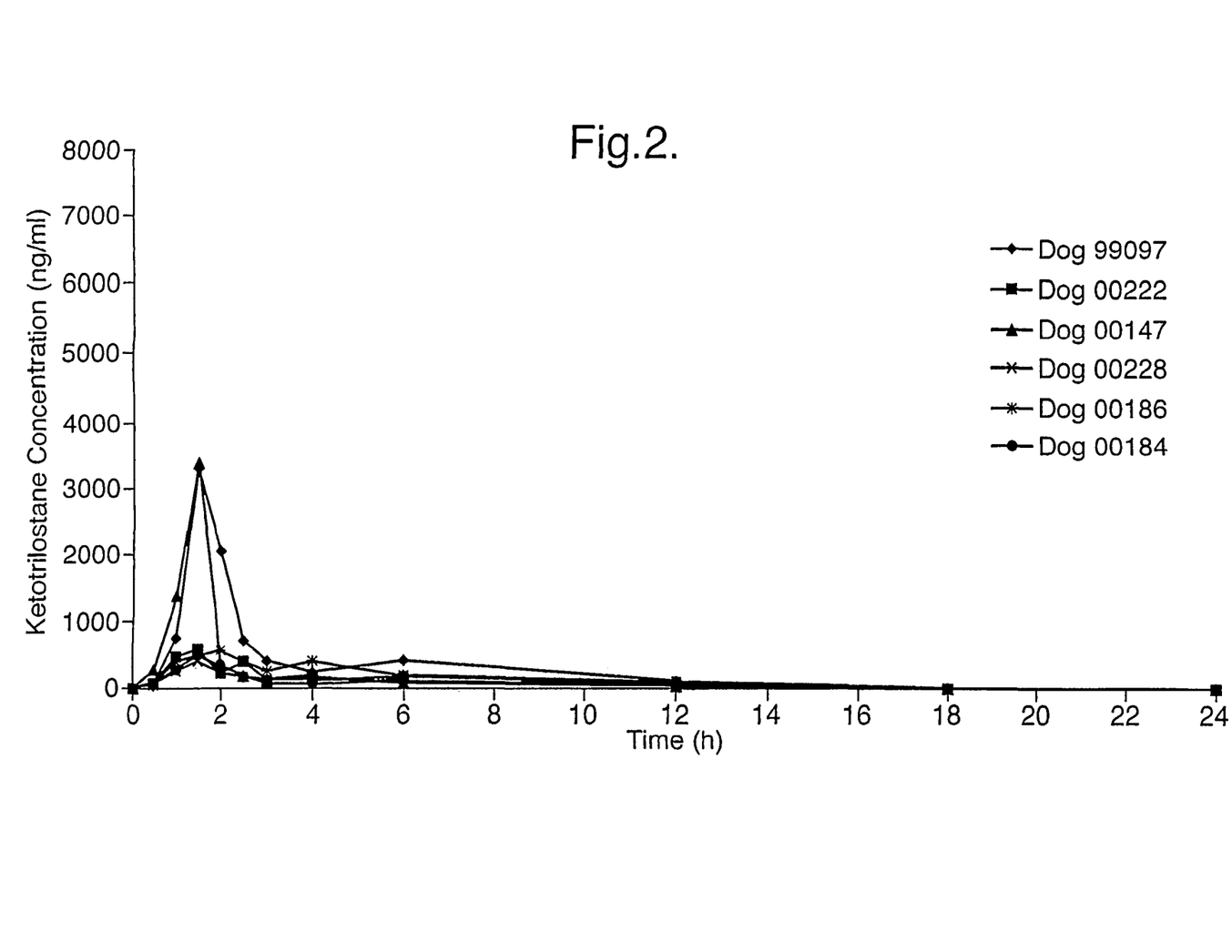
FIG. 2:
Ketotrilostane concentrations in the plasma of 6 dogs: day 0, phase 1 (one 60 mg capsule per day), study no. GB009/01-001.

Serum concentrations of ketotrilostane after single daily dose showing peak at 1-3 hours with rapid elimination thereafter are shown in FIG. 2. The significance of this is that the metabolite, ketotrilostane, is not retained in the body for an extended period of time.

Example 6

Cortisol Levels Post TRH or Dexamethasone Stimulation in Horses

For horses with Cushing's disease, Table 5 shows cortisol levels post TRH stimulation or post Dexamethasone stimulation with single daily dose of trilostane. The results show a lowering of the response to TRH on trilostane. This is similar to the post ACTH stimulation in the dogs. The adrenal gland is not responding to stimulation by pituitary hormone in the same way as before trilostane treatment.

Example 6

Cortisol Levels Post TRH or Dexamethasone Stimulation in Horses

Again in horses with Cushing's disease, Table 6 shows serum cortisol pre- and post-treatment with single daily dose of trilostane. The results show only a small drop in cortisol levels but a clinical response was observed.

Tables

TABLE 1

The mean levels of serum cortisol in horses with equine Cushing's disease before and after treatment with trilostane given orally by intermittent therapy. Each value is the mean of 6 samples taken at 4-hourly intervals over 24 hours. Post-treatment samples were collected after 30 days of trilostane therapy.
HORSES
Mean Cortisol concentrations over 24 hrs.

| PRE-TREATMENT | | POST TREATMENT | |
|---|---|---|---|
| Mean | SD | Mean | SD |
| 100.5 | 9.52 | 108 | 3.8 |
| 142.5 | 26.3 | 203.7 | 31.5 |
| 157.2 | 10.8 | 157.3 | 17.3 |
| 256.5 | 62.8 | 263.3 | 57.6 |
| 147 | 24.4 | 143 | 7.2 |
| 155 | 39.6 | 193 | 41.5 |
| 125.8 | 16.5 | 122.8 | 17.6 |
| 117.3 | 13 | 134.4 | 28.4 |
| 123 | 3.8 | 112 | 21.4 |
| 162.7 | 15.9 | 152.3 | 26.4 |
| 119.6 | 32.1 | 113 | 30.8 |
| 229.3 | 37.4 | 194.7 | 28.3 |
| 92.3 | 11.4 | 94.8 | 8.7 |
| 114.7 | 14.9 | 112.3 | 10.8 |
| 158.8 | 25.4 | 183.3 | 37.8 |
| 165 | 37.5 | 245.5 | 106.3 |
| 126.5 | 14.9 | 158 | 19.2 |
| 170 | 35.7 | 164.5 | 41.4 |
| 175.2 | 30.7 | 160 | 32.8 |
| 153.2 | 28.8 | 149.8 | 51 |

TABLE 2

Results of the mean serum cortisol levels before and after stimulation with TRH and before and after trilostane administered orally by intermittent dosage.

| HORSES Animal | Pre-Treatment | | | Post-Treatment | | | % change |
|---|---|---|---|---|---|---|---|
| | Base | Post TRH | Post Dex | Base | Post TRH | Post Dex | |
| 1 | 193 | 187 | 86 | 288 | 224 | 153 | −15.8 |
| 2 | 127 | 167 | 150 | 160 | 114 | 170 | −60.5 |
| 3 | 181 | 133 | — | 236 | 316 | — | −69 |
| 4 | 131 | 199 | 161 | 116 | 167 | 149 | −8 |
| 5 | 136 | 218 | 122 | 254 | 193 | 118 | −84 |
| 6 | 125 | 142 | 103 | 149 | 93 | 113 | −82 |
| 7 | 104 | 81 | 89 | 127 | 79 | 82 | −16 |
| 8 | 132 | 170 | 85 | 112 | 139 | 81 | −5 |
| 9 | 128 | 183 | 146 | 136 | 158 | 163 | −27 |
| 10 | 57 | 236 | 88 | 65 | 170 | 81 | −233 |
| 11 | 231 | 218 | 157 | 202 | 88 | 50 | −50 |
| 12 | 86 | 160 | 106 | 81 | 150 | 101 | −1 |
| 13 | 98 | 125 | 128 | 100 | 117 | 113 | −10 |
| 14 | 274 | 81 | 98 | 209 | 100 | 138 | 18 |
| 15 | 171 | 222 | 70 | 189 | 138 | 47 | −57 |
| 16 | 143 | 171 | 81 | 121 | 100 | 1 | 1 |

TABLE 3

Post ACTH stimulation test serum cortisol values of dogs after various periods of Trilostane treatment (5-10 mg/k)

| Time-days | 12 | 35 | 81 |
|---|---|---|---|
| (+/−) | 3.9 | 9.7 | 35.0 |
| Cortisol nmol/l | 249 | 231 | 214 |
| (+/−) | 171 | 177 | 158 |
| % pre Trilostane Cortisol | −29.7 | −30.0 | −27.3 |
| No. of dogs | 53 | 59 | 48 |

TABLE 4

Canine serum cortisol nmol/l over 24 hours pre and post Trilostane treatment 5–10 mg/k over 4–21 days

| Time (hrs) | | | | | | | | | | | | | |
|---|---|---|---|---|---|---|---|---|---|---|---|---|---|
| 4 | | 8 | | 12 | | 19 | | 20 | | 24 | | 28 | |
| Trilostane given at 0 hours | | | | | | | | | | | | | |
| pre | post | pre | post | pre | post | pre | post | pre | post | pre | post | pre | post |
| 84 | 5 | 101 | 5 | 94 | 5 | 74 | 52 | 256 | 166 | 85 | 117 | 183 | 147 |
| 104 | 62 | 121 | 5 | 113 | 75 | 131 | 101 | 120 | 105 | 122 | 109 | 140 | 112 |
| 82 | 5 | 88 | 5 | 97 | 83 | 81 | 92 | 86 | 86 | 90 | 51 | 108 | 75 |
| 106 | 10 | 124 | 48 | 127 | 66 | 122 | 63 | 124 | 97 | 97 | 74 | 97 | 86 |
| 88 | 5 | 106 | 5 | 86 | 66 | 86 | 85 | 70 | 61 | — | 66 | — | 53 |
| 215 | 60 | 138 | 171 | 150 | 158 | 203 | 183 | 149 | 154 | 205 | 171 | 86 | 124 |
| 136 | 57 | 118 | 51 | 164 | 197 | 176 | 183 | 117 | 144 | 105 | 144 | 147 | 190 |
| 231 | 5 | 190 | 262 | 147 | 143 | 161 | 183 | 161 | 144 | 212 | 131 | 136 | 174 |
| 135 | 62 | 167 | 183 | 89 | 164 | 61 | 139 | 118 | 108 | 116 | 154 | 112 | 246 |
| 256 | 63 | 203 | 315 | 197 | 318 | 197 | 230 | 186 | 199 | 180 | 246 | 230 | 313 |
| | | | | | | Mean | | | | | | | |
| 144 | 33 | 136 | 105 | 126 | 130 | 129 | 131 | 141 | 126 | 135 | 126 | 138 | 152 |
| | | | | | | +/−* | | | | | | | |
| 65.8 | 27 | 38.7 | 118 | 37.3 | 89.9 | 52.9 | 60.9 | 50.7 | 41.9 | 50.3 | 57.6 | 45.5 | 81.1 |

The only significant difference is at 4 hours post Trilostane

TABLE 5

Horses with Cushings syndrome - cortisol values nmol/l at base, post TRH & post Dex. Tests; before and after 30 days Trilostane treatment, 0.4–1.0 mg/k

| Horse | pre Trilostane | | | | post Trilostane | | | | Different, pre-post | | | |
|---|---|---|---|---|---|---|---|---|---|---|---|---|
| | Base | post TRH | post Dex | % TRH resp | Base | post TRH | post Dex | % TRH resp | Base | post TRH | post Dex | % TRH resp |
| 1 | 193 | 181 | 86 | −6 | 288 | 224 | 153 | −22 | −95 | −43 | −67 | 16 |
| 2 | 127 | 167 | 150 | 31 | 160 | 114 | 170 | −29 | −33 | 53 | −20 | 60 |
| 3 | 131 | 266 | — | 103 | 236 | 316 | — | 34 | −105 | −50 | — | 69 |
| 4 | 131 | 199 | 161 | 52 | 116 | 167 | 149 | 44 | 15 | 32 | 12 | 8 |
| 5 | 136 | 218 | 122 | 60 | 254 | 193 | 118 | −24 | −118 | 27 | 4 | 84 |
| 6 | 125 | 142 | 103 | 14 | 149 | 93 | 113 | −38 | −124 | 49 | −10 | 52 |
| 7 | 104 | 81 | 89 | −22 | 127 | 79 | 82 | −38 | −23 | 2 | 7 | 16 |
| 8 | 132 | 170 | 65 | 29 | 112 | 139 | 81 | 24 | 20 | 31 | −16 | 5 |
| 9 | 128 | 183 | 146 | 43 | 136 | 158 | 163 | 16 | −8 | 25 | −17 | 27 |
| 10 | 57 | 236 | 88 | 314 | 65 | 170 | 81 | 162 | 8 | 66 | 7 | 152 |
| 11 | 231 | 218 | 157 | −6 | 202 | 88 | 50 | −56 | 29 | 130 | 107 | 50 |
| 12 | 86 | 160 | 106 | 86 | 81 | 150 | 101 | 85 | 5 | 10 | 5 | 1 |
| 13 | 98 | 125 | 128 | 28 | 100 | 117 | 113 | 17 | 2 | 8 | 15 | 11 |
| 14 | 274 | 81 | 98 | −70 | 209 | 100 | 138 | −52 | 65 | −19 | −40 | −18 |
| 15 | 171 | 222 | 70 | 30 | 189 | 138 | 47 | −27 | −18 | 84 | 23 | 57 |
| 16 | 143 | 171 | 61 | 20 | 121 | 100 | 1 | −17 | 22 | 71 | 60 | 37 |
| Mean | 141 | 176 | 109 | — | 159 | 147 | 104 | — | −22 | 30 | 5 | 39.2 |
| +/− | 54 | 52 | 34 | | 64 | 61 | 48 | | 58 | 47 | 40 | 41.3 |

The difference between pre and post Trilostane is not significant for base or post Dex. values but is for post TRH values; it is highly significant for the difference in post TRH % response.

TABLE 6

Serum cortisol (nmol/l) in horses with Cushings disease before and after Trilosane
Each value is the mean of 6 samples collected over 24 hours at 4 hourly intervals.
Horses received Trilosane once daily, 0.4-1.0 mg/k, for 30 days

| Pre Trilosane | | Post Trilosane | | |
|---|---|---|---|---|
| Mean | +/− | Mean | +/− | Difference, pre-post |
| 100.5 | 9.5 | 108 | 3.8 | −7.5 |
| 142.5 | 26.3 | 203.7 | 31.5 | −61.2 |
| 157.2 | 10.8 | 157.3 | 17.3 | −0.1 |
| 256.5 | 62.8 | 263.3 | 57.6 | −6.8 |
| 147 | 24.4 | 143 | 7.2 | 4 |
| 155 | 39.6 | 193 | 41.5 | −38 |
| 125.8 | 16.5 | 122.8 | 17.6 | −3 |
| 117.3 | 13 | 134.4 | 28.4 | −17.1 |
| 123 | 3.8 | 112 | 21.4 | 11 |
| 162.7 | 15.9 | 152.3 | 26.4 | 10.4 |
| 119.6 | 32.1 | 113 | 30.8 | 3.6 |
| 229.3 | 37.4 | 194.7 | 28.3 | 34.6 |
| 92.3 | 11.4 | 94.8 | 8.7 | −2.5 |
| 114.7 | 14.9 | 112.3 | 10.8 | 2.4 |
| 158.8 | 25.4 | 183.3 | 37.8 | −24.5 |
| 165 | 37.5 | 245.5 | 106.3 | −80.5 |
| 126.5 | 14.9 | 158 | 19 | −31.5 |
| 170 | 35.7 | 164 | 41 | 5.5 |
| 175.2 | 30.7 | 1 | 32 | 15.2 |
| 153.2 | 28.8 | 149 | 51 | 3.4 |
| Mean | | | | |
| 149.1 | 39.7 | 158.3 | 45.3 | −9.1 +/− 26.9 |

There are no significant difference between the pre and post Trilostane values

The invention claimed is:

1. A method for treating hyperadrenocorticism in a dog comprising administering to the dog an initial once daily dosage of up to 10 mg/kg of trilostane, carrying out an ACTH stimulation test on said dog wherein the post-ACTH stimulation test cortisol concentration of said dog is measured, and administering an increased or twice daily dosage of trilostane to said dog having a post-ACTH stimulation test cortisol concentration greater than 220 nmol/L.

2. The method of claim 1, comprising conducting the ACTH stimulation test every ten days to three months during treatment.

3. The method of claim 1, comprising conducting the ACTH stimulation test every ten days, four weeks, three months or six months during treatment.

4. The method of claim 1, comprising conducting the ACTH stimulation test every three months during treatment.

* * * * *